United States Patent [19]

Sellstedt

[11] 4,061,628

[45] Dec. 6, 1977

[54] INTERMEDIATES FOR PRODUCING SEMI-SYNTHETIC PENICILLINS AND CEPHALOSPORINS AND METHODS OF PRODUCTION

[75] Inventor: John H. Sellstedt, King of Prussia, Pa.

[73] Assignee: American Home Products Corporation, New York, N.Y.

[21] Appl. No.: 378,727

[22] Filed: July 12, 1973

Related U.S. Application Data

[62] Division of Ser. No. 197,142, Nov. 9, 1971, Pat. No. 3,859,298.

[51] Int. Cl.$^2$ .................. C07D 501/04; C07D 499/12
[52] U.S. Cl. .............................. 260/239.1; 424/271; 424/246; 544/22; 544/16; 544/30
[58] Field of Search ...................... 260/239.1, 243 C

[56] References Cited

U.S. PATENT DOCUMENTS 3,809,699  5/1974  Ishimaru .......................... 260/306.7

Primary Examiner—Nicholas S. Rizzo

[57] ABSTRACT

Novel 6-APA, 7-ACA, and 7-ADCA derivatives are described which comprise phosphorylated derivatives of 6-APA, 7-ACA, or 7-ADCA and the corresponding acylated derivatives thereof. The novel compounds are prepared by the reaction of 6-APA, 7-ACA, 7-ADCA or a salt thereof with a phosphorus halide in the presence of an acid acceptor and subsequently acylating the thus formed phosphorylated compound, to form a phosphorylated acylated derivative which upon hydrolysis with water splits off the protective group(s) to provide the corresponding semi-synthetic penicillin or cephalosporin having useful antibacterial activity.

15 Claims, No Drawings

INTERMEDIATES FOR PRODUCING SEMI-SYNTHETIC PENICILLINS AND CEPHALOSPORINS AND METHODS OF PRODUCTION

This application is a division of application Ser. No. 197,142 filed Nov. 9, 1971, now U.S. Pat. No. 3,859,298.

This invention relates to novel phosphorylated 6-APA, 7-ACA, and 7-ADCA derivatives, acylated derivatives thereof and the process for their production.

One aspect of the present invention relates to the production of semi-synthetic penicillins and cephalosporins in high yields from compounds such as 6-amino penicillanic acid, 7-amino cephalosporanic acid, and 7-amino-3-desacetoxy cephalosporanic acid.

Another aspect of the present invention relates to the acylation of novel phosphorylated 6-amino penicillanic acids, 7-amino cephalosporanic acids, and 7-amino-3-desacetoxy cephalosporanic acids in the absence of an acid acceptor.

Yet another aspect of the present invention relates to novel acylated and phosphorylated derivatives of 6-amino penicillanic acid 7-amino cephalosporanic acid, 7-amino-3-desacetoxy cephalosporanic acid and related compounds.

These and other aspects of the present invention will become apparent from the following description.

In its broadest aspects the present invention covers compounds having the following structure:

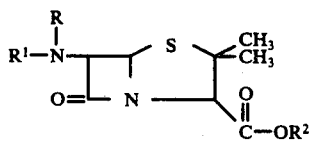

A and

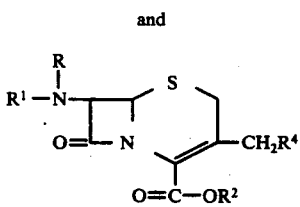

B wherein:
R is a member selected from the class consisting of hydrogen and an organic acyl radical; $R^1$ is selected from the class consisting of hydrogen and a radical of the formula $$R^6-\overset{R^5}{\underset{|}{P}}- ;$$

with the proviso that R and $R^1$ are not both hydrogen; $R^2$ is a member selected from the class consisting of $R^1$, alkali metal (e.g. Na, K) and a tertiary amine;

$R^4$ is a member selected from the class consisting of hydrogen, (lower)alkanoyloxy containing 2 to 8 carbon atoms, and a quaternary ammonium radical.

$R^5$ and $R^6$ are each selected from the class consisting of (lower) alkyl, aryl, halo(lower)alkyl, aryl(lower)alkyl; and $R^5$ and $R^6$ may be joined together to form with phosphorus, the ring

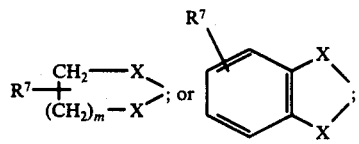

wherein X is selected from the class consisting of oxygen, $CH_2$ and sulfur; $m$ is an interger from 1 to 6; $R^7$ is hydrogen or (lower)alkyl.

The preferred novel compounds of the present invention are those having the following formulae:

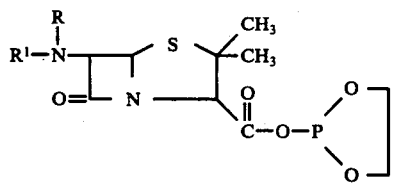

and

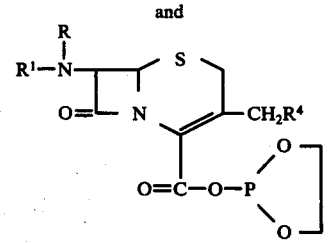

wherein:
R is selected from the class consisting of hydrogen and organic acyl;
$R^1$ is selected from the class consisting of hydrogen and

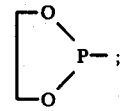

with the proviso that R and $R^1$ are not both hydrogen;
$R^4$ is selected from the class consisting of hydrogen and acetoxy.

The term "(lower)alkyl" as employed herein alone or in conjunction with other designated groups is intended to encompass straight chain or branch chain alkyl groups consisting of from one through six carbon atoms (e.g. methyl, ethyl, propyl, butyl, isobutyl, hexyl, 2-ethylpropyl, etc.)

The term "halogen" as used herein is intended to encompass chlorine, bromine, iodine and fluorine. The term "aryl" encompasses monocyclic and bicyclic rings having six to ten ring carbon atoms such as phenyl, naphthyl, etc. The term "aryl(lower) alkyl" is illustrated by benzyl, phenethyl, etc.

The term "(lower)alkanoyloxy" is illustrated by acetoxy, propionoyloxy and butanolyloxy. The term "quaternary ammonium" is illustrated by pyridinium, quinolinium, picolinum, etc. The term "tertiary amine" is illustrated by any of the well-known radicals such as triethylamine, tribenzylamine, N-ethylpiperidine which are described in the penicillin and cephalosporin art as capable of forming an amine salt with the carboxyl group.

The acyl group defined by R is derived from an organic carboxylic acid or a suitable functional reactive derivative thereof.

When R is acyl, the preferred acyl radicals are selected from groups having the following formulae:

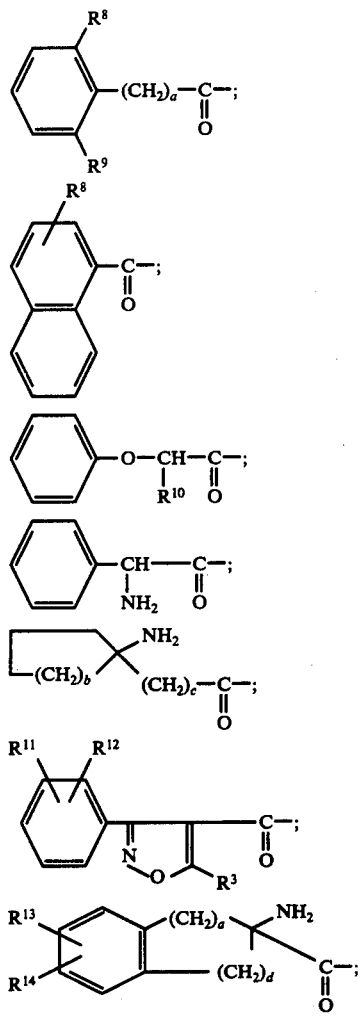

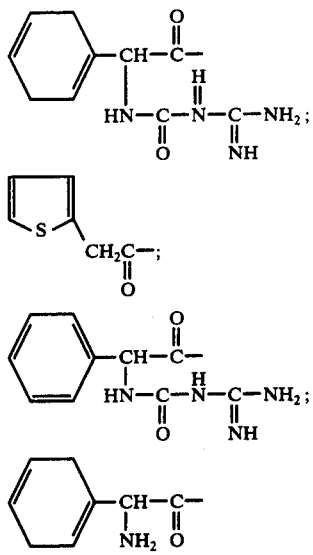

wherein:
R³ is selected from the class consisting of hydrogen, (lower)alkyl and phenyl; R⁸ and R⁹ are selected from the group consisting of hydrogen and (lower)alkoxy;
R¹⁰ is selected from the class consisting of hydrogen, (lower)alkyl and phenyl;
R¹¹ and R¹² are selected from the class consisting of hydrogen and halogen;
R¹³ and R¹⁴ are selected from the class consisting of hydrogen, halogen, (lower)alkyl, (lower)alkoxy, phenyl and phenoxy;
$a$ is an interger from 0 to 1; $b$ is an interger from 0 through 5;
$c$ is an interger from 0 through 2; $d$ is an interger from 1 through 3, with the proviso that when $a$ is 0, $d$ is greater than 1, and when $a$ is 1, $d$ is less than 3.

Semi-synthetic penicillins and cephalosporins may be prepared according to the following flow diagrams, using 6-APA and 7-ACA respectively, as illustrative starting materials.

DIAGRAM A

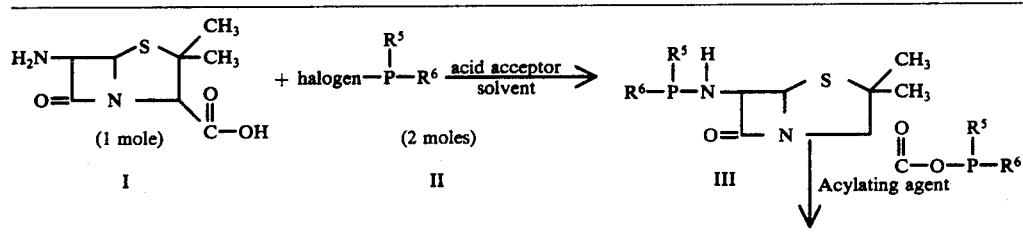

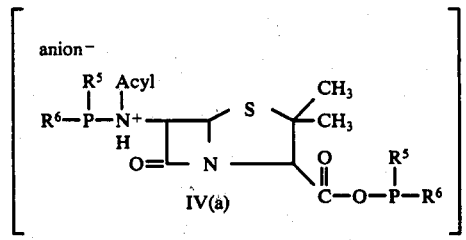

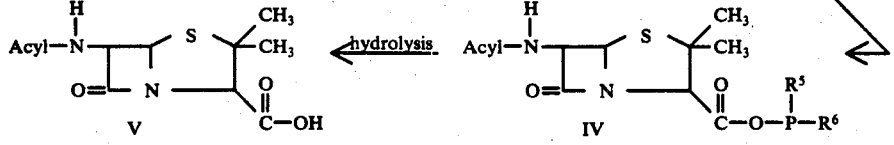

DIAGRAM B

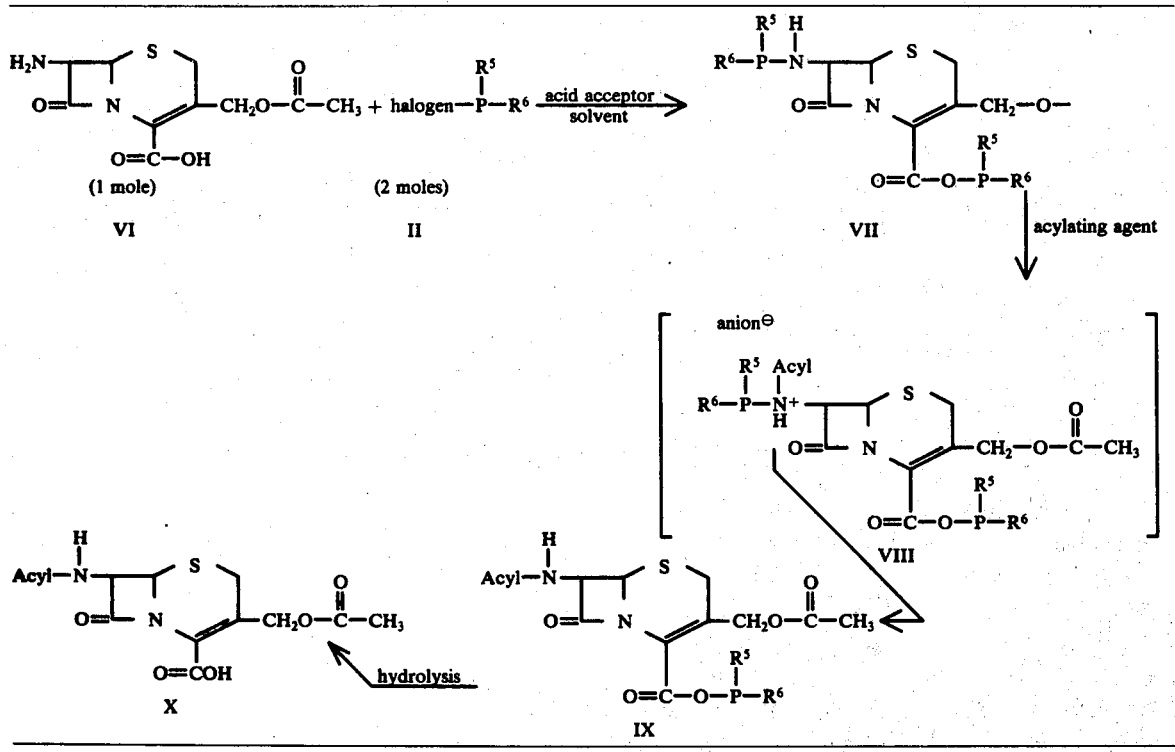

In the foregoing process the starting material (e.g. 6-APA, 7-ACA or 7-ADCA) which may be obtained by any number of procedures described in the art (e.g. See U.S. Pat. Nos. 3,499,909 and 2,941,995) is reacted with a phosphorus halide of formula II in the presence of inert organic solvent and an acid acceptor to form a compound of formula III or VII respectively. This reaction is preferably carried out at a temperature above $-10°$ C. and not higher than about $-25°$ C. The molar ratio of an acid binding agent to a starting material such as 6-APA is about 0.75:2 and the molar ratio of acid binding agent to a compound of formula II is 1:1.

Suitable acid binding agents are tertiary amines such as triethyl amine, dimethylaniline, quinoline, pyridine, lutidine, alkali metal carbonates; alkaline earth carbonates or other acid binding agents known in the art. The preferred acid binding agent is a strong tertiary amine. As used herein "strong amines" are those characterized by having dissociation constants in the range of from $10^{-3}$ to $10^{-6}$ or having comparable basicity, as distinguished from "weak amines" which are characterized by having dissociation constants in the range of from $10^{-8}$ to $10^{-11}$.

A wide range of anhydrous non-hydroxylic organic solvents are useful in the reaction of 6-APA or 7-ACA with a phosphorylating agent including hydrocarbons such as benzene and toluene; chlorinated solvents such as methylene chloride, chloroform and chlorobenzene; ethers such as diethyl ether, dioxane, tetrahydrofuran; and other conventional solvents such as methylisobutylketone, dimethylformamide, ethyl acetate, acetonitrile, etc.

The reaction between 6-APA, 7-ACA, or 7-ADCA and a phosphorus halide is carried out preferably at a temperature at which the reaction proceeds to completion in a reasonably short time period, i.e. between −10° C. and +10° C.

A compound of formula III and VII prepared according to this invention can be isolated by removing the hydrohalide base by filtration and distillation of the solvent, or if the intermediate is to be converted at once to a penicillin or cephalosporin, the reaction mixture can be acylated directly without filtration or concentration.

The product or products obtained from the reaction of a compound of formula I or VI with a phosphorylating agent is dependent on the molar ratio of the reactants as to whether an anhydride of the penicillanic acid is formed. Thus, if the molar ratio of a compound of formula II to formula I is greater than 1:1, the predominant material obtained is a compound of formula III, particularly as the molar ratio increases to about 2:1 and higher. On the other hand where the molar ratio is 1:1 or less (e.g. 0.5:1), the predominant compound is

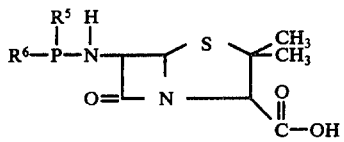

with the amount of a compound of formula III becoming smaller as the molar ratio of a compound of formula II is decreased in relation to the amount of 6-APA.

The preferred molar ratio of phosphorylating agent to the starting material such as a compound of formula I or VI is greater than 1:1, preferably at least 2:1.

The fact that mixtures of phosphorylated compounds can be produced under certain reaction conditions does not interfere with the process of acylation and subsequent formation of the desired semi-synthetic penicillin or cephalosporin.

Novel phosphorylated acylated compounds within the scope of formula A and B may be prepared by the acylation of a compound of formula III or VII in accordance with the reaction sequence shown above in diagrams A and B, respectively.

Suitable acylating agents include carboxylic acid halides, carboxylic acid anhydrides, mixed anhydrides with other carboxylic or inorganic acids; esters such as thiol esters and phenol esters; lactones; and carboxylic acids with carbodiimides or N,N¹-carboxyldiimidazoles.

Illustrative of some specific preferred acylating agents are phenoxyacetyl chloride, 2,6-dimethoxybenzoyl chloride, benzene sulfonyl chloride, 2-phenoxypropionyl chloride, 2-phenoxy-butyl chloride, D(-)phenylglycyl chloride HCl, 1-aminocyclopentane-carboxylic acid chloride HCl, 1-aminocyclohexanecarboxylic acid chloride HCl, 2-amino-2-carboxyindane acid chloride HCl, 2-ethoxy naphthoyl bromide and 3-(2,6-dichlorophenyl)-5-methyl-isoxazole carbonyl chloride, etc.

In carrying out the acylation step, it has been surprisingly found that an acid acceptor need not be present during the reaction. Heretofore such a reagent was deemed essential for successfully carrying out the acylation procedure as illustrated by U.S. Pat. Nos. 3,595,855; 3,249,622. In addition, where a strong amine is used in reacting a compound of formula I with a compound of formula II, it is desirable to avoid the presence of any excess strong amine because the strong amine has a deleterious effect on the yield of semi-synthetic penicillin produced. The acylation process is carried out in the presence of an inert anhydrous organic solvent. Suitable solvents may be the same as earlier exemplified for the reaction producing the phosphorylated derivatives of 6-APA, 7-ACA, 7-ADCA, etc.

The acylated penicillins and cephalosporins of formulae IV and IX are readily hydrolyzed by treating with water, to split off the protective group from the amino group and the carboxyl group to form a semi-synthetic penicillin or cephalosporin embraced by formulae V and X, respectively.

The acylation of a compound of formula III or VII first results in the formation of an intermediate of formula IV(a) or VIII, respectively. These intermediates repidly convert to a compound of formula IV and IX, respectively as a result of expulsion of

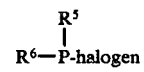

from the nitrogon atom. This expulsion is due to the presence of an anion (e.g. Cl⁻) upon formation of the intermediate of formula IV(a) or VIII, respectively, which attacks the phosphorus atom linked to the nitrogen. It is possible that the presence of a weak base during the acylation would bind the anion and thereby avoid the expulsion of

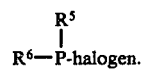

In the latter case hydrolysis of a compound of formula IV(a) or VIII, respectively, would result in direct formation of a compound of formula V or X, rather than intermediate IV or IX.

The hydrolysis is carried out at a pH between 0.5 and 2 at a temperature below about 15°, preferably between 0° and 5° C. The hydrolysis is carried out by treatment with water.

Where the acylating agent used is in the form of an acid addition salt, the penicillin or cephalosporin of formula V or X is recovered upon hydrolysis as an acid addition salt (e.g. chloride) which may then be converted to the free base by methods well known in the art. In the event the ultimate penicillin to be obtained is α-aminobenzyl penicillin (ampicillin), it has been found advantageous to change the chloride to an aryl sulfonic acid salt of the aminopenicillin either by adding an appropriate sulfonic acid to the reaction mixture comprising the selected organic solvent and water, or to the aqueous extracts separated as described immediately above. In this connection, a 25% excess of the sulfonic acid has been used to advantage in preparing the corresponding salt of ampicillin.

The aryl sulfonic salt of the α-aminobenzyl penicillin may then be converted to the penicillin per se by reaction with a base such as triethylamine or diethylamine in approximately 85% isopropanol. In the case of ampicillin specifically, the sulfonic acid salt, wet with water and ethyl acetate, may be added to isopropanol containing a molar equivalent of triethylamine at 75°–80° C., whereby the anhydrous form of ampicillin described and claimed in U.S. Pat. No. 3,144,445 is formed and collected by filtration from the hot mixture.

Alternatively, the corresponding penicillin may be obtained, but in hydrated form, by raising the pH of the aqueous reaction mixture containing the hydrochloride salt of said penicillin to the iso-electric point.

The starting materials defined by formula II may be prepared by procedures described in the literature. For example, the preparation of 2-chloro-1,3,2-dioxaphospholane is described by Lucas et al., J. Am. Chem. Soc. 72, 5491–5497 (1950). Other compounds within the scope of formula II may be prepared by the procedures described by Brown et al., J. Chem. Soc. 878–881 (1970).

The following examples are given by way of illustration and are not to be construed as limitations of this invention.

EXAMPLE 1

D(-)α-aminobenzylpenicillin

6-Aminopenicillanic acid (10.81 g, 0.05 mole) is stirred for ½ hr. in 100 ml. of dichloromethane at 0°–5° C. containing 13.85 ml. of triethylamine. At 0°–5° C., a solution of 12.65 g. (0.1 mole) of 2-chloro-1,3,2-dioxaphospholane in 50 ml. of dichloromethane is added over 1 hr., and the mixture is stirred an additional ½ hr. at 0°–5° C. The resulting product is 6-(1,3,2-dioxaphospholan-2-yl amino) penicillanic acid, 1,3,2-dioxaphospholan-2-yl ester. D-(-)phenylglycyl chloride hydrochloride (10.63 g., 0.05 mole) is added to the stirred mixture over 2 min., and stirring is continued for ½ hr. at 0°–5° C. under nitrogen. The cooling bath is removed and the temperature is allowed to go to 17° C. and held at this temperature for a total acylation time of 3 hr. The resulting acylated product is 6-(2-amino-2-phenylacetamido)penicillanic acid, 1,3,2-dioxaphospholan-2-yl ester. The mixture is poured into 300 ml. of water at 0°–5° C. and stirred for 15 min., with the pH going to 0.7. Celite is added, the mixture is filtered, and the filtrate is separated and the water layer (340 ml.) is bioassayed vs. S. Lutea. The addition of 5 ml. of this solution to 245 ml. of 1% pH 6 buffer gives an assay value of 700 γ/ml. of ampicillin.

The β-naphthalene sulfonic acid salt is prepared from the 340 ml. of solution by adding ethyl acetate (40 ml.) and cooling to 0°–10° C. followed by addition of 29.4 g. of a 37,68% solution of β-naphthalene sulfonic acid over 10 min. and holding the pH at 1.5 to 1.7 with the addition of 5N sodium hydroxide. This mixture is stirred overnight at 5° (filtered, stirred in 60 ml. of ethyl acetate for 5 min., filtered and sucked dry, giving 27.3 g. the β-naphthalene sulfonic acid salt of D(-)α-aminobenzylpenicillin. It was bioassayed vs. S. Lutea indicating the presence of 560 γ/mg. of ampicillin.

EXAMPLE 2

1-aminocyclohexane penicillin

6-Aminopenicillanic acid (43.25 g., 0.7 mole) is stirred in dichloromethane (400 ml). containing triethylamine (55.6 ml., 0.4 mole) at room temperature until solution is complete. The temperature is lowered to 0°–5° C., and 50.6 g. (0.4 mole) 2-chloro-1,3 2-dioxophospholane in 200 ml. of dichloromethane is added over 1 hr., and stirring is continued at 0°–5° C. for ½ hr. 1-aminocyclohexanecarboxylic acid chloride hydrochloride (40 g., 0.2 mole) is added, and the mixture is stirred while the internal temperature is allowed to slowly go to 10° C. over ½ hr., and the reaction is continued for an additional 2½ hr. at 10° C. The mixture is poured into 200 ml. of cold (0°–5° C.) water and the mixture is stirred in an ice bath for 15 min. Isopropanol (160 ml.) and celite (15 g.) are added, the mixture is filtered by suction, and the cake is washed with 40 ml. of isopropanol. The two-phase filtrate is poured into a 2 liter round bottom 3-neck flask, and while stirring at 15°–20° C., the pH is raised to 5.4–5.5 with 5N NaOH, giving white crystals of dihydrate of the above tilted compound.

EXAMPLE 3

D(-)-α-aminobenzylpenicillin

6-Aminopenicillanic acid (43.25 g., 0.2 mole) is stirred in dichloromethane (400 ml.) containing triethylamine (55.6 ml., 0.4 mole) at room temperature until solution is complete. The temperature is lowered to 0°–5° C., and 50.6 g. (0.4 mole) 2-chloro-1, 3,2-dioxophospholane in 200 ml. of dichloromethane is added over 1 hr., and continue to stir at 0°–5° C. for ½ hr. D(-)Phenylglycyl chloride hydrochloride (43.6 g., 0.2 mole) is added over about 1 min., and the mixture is stirred at 0°–5° C. for ¾ hr. The ice bath is lowered so that only the lower 1–2 cm. of the flask is in the ice water, and the internal temperature is allowed to slowly (about 25 min.) go to 10° C., and then held at this point for a total temperature raising time and reaction time of 2 hr. The mixture is poured into 800 ml. of room temperature water, and the flask is rinsed with 200 ml. of water. The mixture is stirred with the vessel in an ice-bath for 15 min., Super Cel is added, the mixture is filtered by suction, and the cake is washed with 200 ml. water. The layers are separated, and the aqueous phase is placed in a 2 liter round bottom flask containing 200 ml. ethyl acetate. The internal temperature is lowered to 0°–10° C. and the pH is adjusted to 2 by the addition of 5N sodium hydroxide. Then 100 ml. of a 37.7% β-naphthalene sulfonic acid solution is added in about 10 minutes while keeping the pH at 1.5 to 1.7 with 5N NaOH. After stirring 6 hr. at 0°–5° C., and no stirring for 12 hr., the mixture is filtered, and the cake is washed with about 100 ml. of cold pH 2water. After sucking as dry as possible the cake is stirred in 250 ml. of ethyl acetate for 5 minutes, the mixture is filtered, and the cake is washed with 2 × 50 ml. ethyl acetate, giving 137 g. of the above titled product. A portion of the sample is dried indicating 53.5% NVM with a corresponding yield of 66%, but bioassay vs. S. Lutea indicates 380 γ/mg. with a corresponding yield of 75%. This material is converted to anhydrous ampicillin in 80% yield by the standard isopropanol/-triethylamine procedure as described in U.S. Pat. No. 3,487,073.

EXAMPLE 4

D(-)-α-aminobenzylcephalosporin

In a manner similar to the process for preparation of ampicillin in Example 1, but using 7-amino-cephalosporanic acid (54.6 g., 0.2 mole) instead of 6-aminopenicillanic acid, D(-)-α-aminobenzylcephalosporin is isolated by adjusting the pH of the aqueous phase, obtained after filtration, to about 5.75.

EXAMPLE 5 naphthalene sulfonic acid salt of D(-)-α-aminobenzylpenicillin

6-Aminopenicillanic acid (21.7 g., 0.1 mole) is stirred in dichloromethane (200 ml.) at 0°–5° C., and 14.0 ml. (0.1 mole) of triethylamine is added, and the mixture is stirred for ½ hr. At 0°–5° C., a solution is dripped in of 2-chloro-1,3,2-dioxophopholane (12.7 g., 0.1 mole) in dichloromethane (100 ml.) over a 1 hr. period and stirring is continued at 0°–5° C. for ½ hr. D-(-)-phenylglycyl chloride hydrochloride (21.3 g., 0.1 mole) is added all at once and the mixture is stirred at 0°–5° C. for 30 min. The ice bath is lowered so that only the lower 1–2 cm. of the flask is in the ice water, and the internal temperature is allowed to slowly go to 10° C. over about 2 hr., and the mixture is poured into 450 ml. of room temperature water, and the flask is rinsed with 60 ml. of water. The mixture is stirred with the vessel in ice bath for 15 min., Super Cell is added, the mixture is filtered by suction, and the cake is washed with 100 ml. of water. The layers are separated, and the aqueous phase is placed in a 1 liter round bottom flask containing 100 ml. of ethylacetate. The internal temperature is lowered to 0°–10° C. and the pH is raised to 2 by the addition of 5N NaOH. The 60 g. of a 37% β-naphthalene sulfonic acid solution is added within 5 to 10 min. while keeping the pH at 1.5 to 1.7 with 5N NaOH. After stirring overnight at 0°–5° C., the mixture is filtered, and the cake is washed with cold pH2water (30 ml.). After sucking as dry as possible the cake is stirred in 125 ml. of ethyl acetate for 5 min., the mixture is filtered, and the cake washed twice with ethyl acetate, giving 38.2g. of the β-naphthalene sulfonic acid salt of D(-)-α-aminobenzylpenicillin. A portion of the sample is dried indicating the pressure of 6.36 g. of NVM, with a corresponding 44% yield of the above titled product.

EXAMPLE 6

Following the procedure of Example 1, a series of phosphorylated penicillin compounds are prepared by reacting 2 moles of a phosphorylating agent of formula C with one mole of 6-APA to produce a compound of formula D.

| | $R^5$, | $R^6$ | X | $R^5$, | $R^6$, |
|---|---|---|---|---|---|
| (a) | $CH_3$ | $CH_3$ | Cl | $CH_3$ | $CH_3$ |
| (b) | φ | φ | Cl | φ | φ |
| (c) | $CH_2\phi$ | $CH_2\phi$ | Br | $CH_2\phi$ | $CH_2\phi$ |
| (d) | —S—S— | | Cl | —S—S— | |
| (e) | $C_2H_5$ | $C_2H_5$ | Cl | $C_2H_5$ | $C_2H_5$ |
| (f) | o-O-O- (catechol) | | Cl | o-O-O- | |
| (g) | —CH₂—CH₂— | | Cl | —CH₂—CH₂— | |

EXAMPLE 7

Following the procedure of Example 4, a series of phosphorylated penicillin compounds are prepared by reacting 2 moles of a phosphorylating agent of formula C with one mole of 7-ACA or 7-ADCA to produce a compound of formula E.

| | $R^5$, | $R^6$ | X | $R^2$, | $R^5$, | $R^6$, | X |
|---|---|---|---|---|---|---|---|
| (a) | $CH_3$ | $CH_3$ | Cl | H | $CH_3$ | $CH_3$ | Cl |
| (b) | —O—O— | | Br | H | —O—O— | | Br |
| (c) | φ | φ | F | H | φ | φ | F |
| (d) | $CH_2\phi$ | $CH_2\phi$ | Cl | OCCH₂ (O=) | $CH_2\phi$ | $CH_2\phi$ | Cl |

EXAMPLE 8

Following the procedure of Example 1, a series of phosphorylated penicillin compounds are prepared by reacting 0.5 mole of a phosphorylating agent of formula C with one mole of 6-APA to produce a compound of formula F.

| | $R^5$, | $R^6$ | X | $R^5$, | $R^6$, |
|---|---|---|---|---|---|
| (a) | $CH_3$ | $CH_3$ | Cl | $CH_3$ | $CH_3$ |
| (b) | φ | φ | Cl | φ | φ |
| (c) | $CH_2\phi$ | $CH_2\phi$ | Br | $CH_2\phi$ | $CH_2\phi$ |
| (d) | —S—S— | | Cl | —S—S— | |
| (e) | $C_2H_5$ | $C_2H_5$ | Cl | $C_2H_5$ | $C_2H_5$ |
| (f) | o-O-O- | | Cl | o-O-O- | |

EXAMPLE 9

Following the procedure of Example 4 a series of phosphorylated cephalosporin compounds are prepared by reacting 0.5 mole of a phosphorylating agent of formula C with one mole of 7-ACA or 7-ADCA to produce a compound of formula G.

| | $R^5$, | $R^6$ | X | $R^2$, | $R^5$, | $R^6$, |
|---|---|---|---|---|---|---|
| (a) | $CH_3$ | $CH_3$ | Cl | H | $CH_3$ | $CH_3$ |

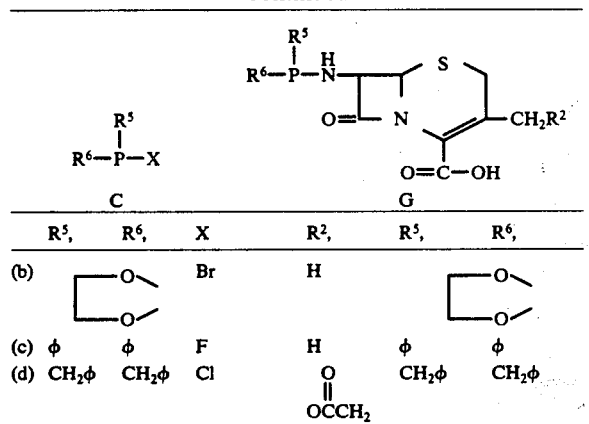

| R⁵, | R⁶, | X | R², | R⁵, | R⁶, |
|---|---|---|---|---|---|
| (b) | —O—O— (dioxolane) | Br | H | | —O—O— (dioxolane) |
| (c) | φ | φ | F | H | φ | φ |
| (d) | CH₂φ | CH₂φ | Cl | $\underset{\text{OCCH}_2}{\overset{O}{\parallel}}$ | CH₂φ | CH₂φ |

EXAMPLE 10

Following the procedure of Example 1, the following acylating agents are used in place of D(-)phenyl glycine chloride hydrochloride to obtain the following acylated phosphorylated penicillin derivatives. Those having an amino group are obtained as the hydrochloride salt.

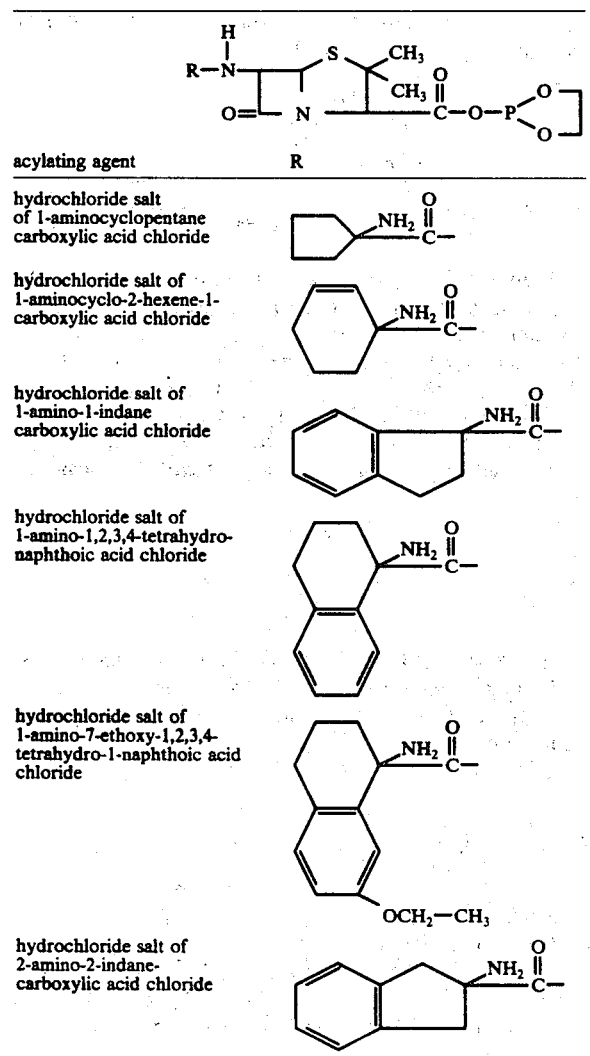

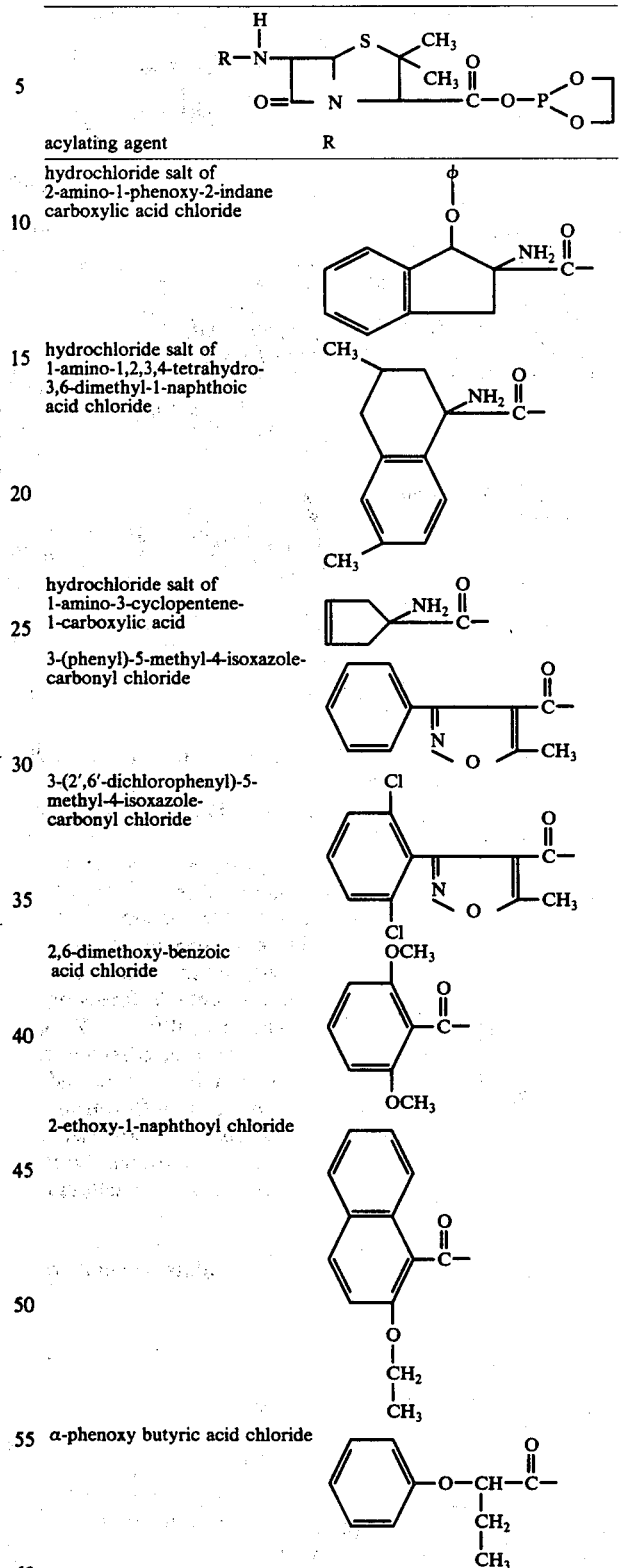

EXAMPLE 11

Following the procedure of Example 4, the acylating agents identified below are used to obtain the following acylated phosphorylated cephalosporins. Those having the amino group are obtained as the hydrochloride salt.

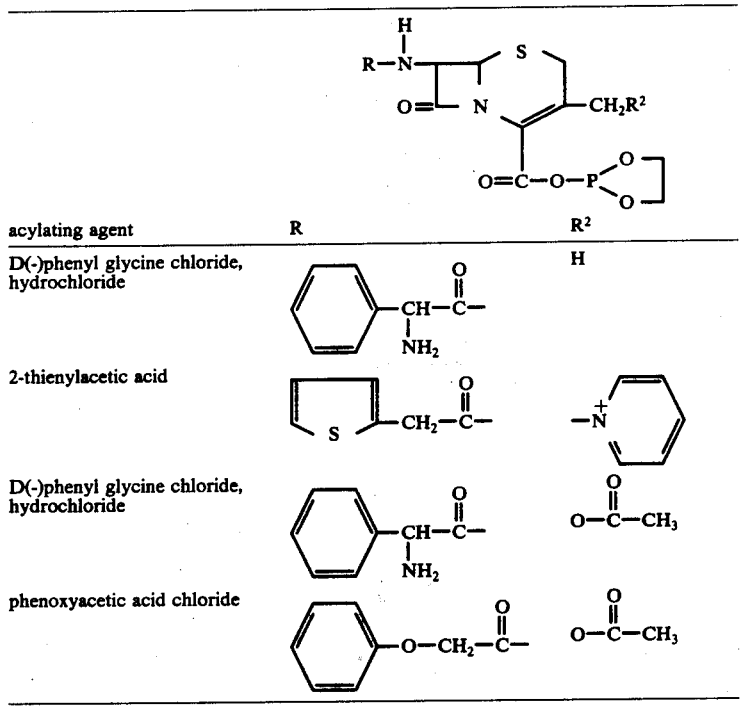

It is to be understood that the only limitation on the acyl radical of the synthetic penicillins and cephalosporins is that they be essentially non-toxic upon in vitro or in vivo application.

The synthetic penicillins and cephalosporins prepared from the intermediates of the present invention have acitivity against gram positive and/or gram negative bacteria and may be utilized in pharmacological compositions in association with pharmacologically acceptable carrier, e.g. in suitable injectable forms, including solutions and suspensions; or orally as tablets, capsules, and the like, utilizing conventional solvents, suspensoids, excipients, and the like. These compounds may be admininstered orally or parenterally. Naturally, the dosage of these compounds will vary somewhat with the form of administration and the particular compound chosen. Further, it will vary with the particular subject under treatment.

What is claimed is:

1. In a process for producing penicillins or cephalosporins of the formula:

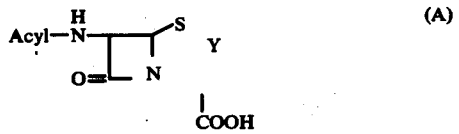 (A)

wherein:

Y is 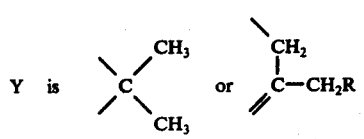

and R is hydrogen or acetoxy which comprises (a) reacting a salt from the group consisting of the alkali metal salts and tertiary amine salts of 6-aminopenicillanic acid or 7-aminocephalosporanic acids of the formula:

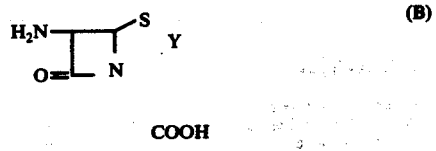 (B)

wherein Y is the same as in formula A above with a protective forming agent in the presence of an acid binding agent, then (b) reacting the resulting compounds with an acylating agent from a reactive derivative of a carboxylic acid to form the corresponding N-acyl derivatives, the improvement consisting essentially of employing as the protective forming agent a three valence phosphorus compound of the formula:

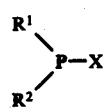

wherein $R^1$ and $R^2$ are lower alkyl, phenyl, halo(lower)alkyl or phenyl(lower)alkyl; or $R^1$ and $R^2$ together jointly form a ring compound selected from the group consisting of:

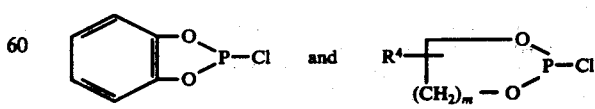

wherein m is a whole number from 1 to 2 and $R^4$ is selected from hydrogen and methyl; X signifies a halogen atom subjecting the N-acyl compounds of (b) above to hydrolysis to obtain the compounds of formula A, above.

2. A process for preparing a penicillin or cephalosporin having antibacterial activity against gram positive and/or gram negative microorganisms, which comprises:

a. reacting a member selected from the class consisting of a compound of the formula:

$$\underset{O=\!\!=\!\!\!\underset{N}{\overset{H_2N-}{\big|}}\!\!\!\!\!\!\!\!\!\!\!\!\!\!\!\!\!\!\!\!\!\!\!\!\!\!\!\!\underset{C-OR^2}{\overset{S}{\diagdown}}\!\!\!\!\!\!\!\!\!\!\!\!\!\!\!\!\!\!\!\!\!\!\!\!\!\!\!\!\!\!\!\!\overset{CH_3}{\underset{CH_3}{\big\langle}}\!\!\!\!\!\!\!\!\!\!\!\!\!\overset{O}{\underset{\|}{}}}\quad A$$

and $$B$$

wherein $R^2$ is selected from the class consisting of hydrogen, alkali metal and tertiary amine; $R^4$ is selected from the class consisting of hydrogen, (lower)alkanoyloxy containing 2 to 8 carbon atoms, and a quaternary ammonium radical; with a phosphorylating agent of the formula $$\text{halogen-}\underset{R^6}{\overset{R^5}{\underset{|}{P}}}$$

in the presence of an acid binding agent to form a phosphorus anhydride derivative of said compound of formula A or B, wherein $R^5$ and $R^6$ are each selected from the class consisting of (lower)alkyl, phenyl, naphthyl, halo(lower)alkyl, phenyl(lower)alkyl and naphthyl(lower)alkyl; $R^5$ and $R^6$ when joined together with the phosphorus atom form the ring or X is selected from the class consisting of oxygen, methylene and sulfur; m is an interger from 1 to 6; and $R^7$ is selected from the class consisting of hydrogen and (lower)alkyl;

b. reacting said phosphorus anhydride derivative obtained in step (a) with an acylating agent selected from an organic carboxylic acid and a reactive functional derivative of said organic carboxylic acid to form the corresponding N-acyl derivative of said phosphorus anhydride obtained in step (a); and c. subjecting said N-acyl compound obtained in step (b) to hydrolysis to obtain a compound selected from those of the formula:

and and an acid addition salt thereof.

3. A process according to claim 2 wherein said molar ratio of said phosphorylating agent to said compound of formula A or B is at least 0.5:1.

4. A process according to claim 3 wherein said acid binding agent is a tertiary amine.

5. A process according to claim 3 wherein said phosphorylating agent is a compound of the formula:

wherein: X is oxygen.

6. A process according to claim 5 wherein said phosphorylating agent is a 2-halo-1,3,2-dioxaphospholane.

7. A process according to claim 6 wherein said reaction of said phosphorylating agent with a compound of formula A or B is carried out at a temperature of between about $-10°$ and $+25°$ C.

8. A process for preparing a penicillin having antibacterial activity against gram positive and/or gram negative microorganism, which comprises:

a. reacting 6-aminopenicillanic acid with a phosphorylating compound of the formula:

wherein: $R^7$ is selected from the class consisting of hydrogen and lower alkyl; in the presence of an acid binding agent to form a phosphorus anhydride derivative of 6-aminopenicillanic acid, the molar ratio of said phosphorylating compound to 6-aminopenicillanic acid being at least about 1:1;

b. reacting said phosphorus anhydride derivative of said 6-aminopenicillanic acid with an acylating agent which is a reactive functional derivative of an organic carboxylic acid to form an N-acylated compound of the formula:

and; (c) subjecting said N-acylated compound to hydrolysis to obtain a compound selected from the class consisting of:

and an acid addition salt thereof.

9. A process according to claim 8 wherein said acid binding agent is a strong tertiary amine.

10. A process according to claim 9 wherein said acylating reagent reacted with said phosphorus anhydride derivative of 6-aminopenicillanic acid contains an acyl group selected from the class consisting of:

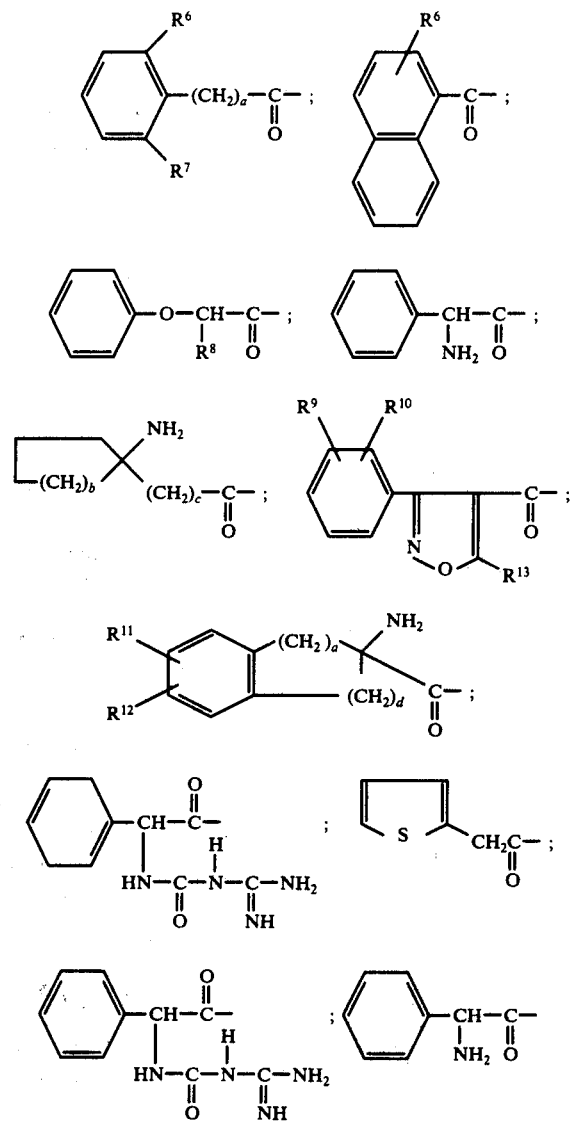

wherein:
R⁶ and R⁷ are selected from the group consisting of hydrogen and (lower)alkoxy;
R⁸ is selected from the group consisting of hydrogen, (lower)alkyl and phenyl;
R⁹ and R¹⁰ are selected from the group consisting of hydrogen and halogen;
R¹¹ and R¹² are selected from the group consisting of hydrogen, halogen, (lower)alkyl, (lower)alkoxyl phenyl and phenoxy;
R¹³ is selected from the class consisting of hydrogen, (lower) alkyl and aryl;

a is an interger from 0 to 1; b is an interger from 0 through 5;
c is an interger from 0 to 2; d is an interger from 1 through 3, with the proviso that when a is 0, d is greater than 1, and when a is 1, d is less than 3.

11. A process according to claim 9 wherein said acylating agent is selected from the class consisting of D(-)phenylglycyl chloride, hydrochloride and 1-amino-1-cyclohexane carboxylic acid chloride hydrochloride.

12. A method of preparing an acid addition salt of D(-)α-aminobenzyl penicillin which comprises reacting 2-chloro-1,3,2-dioxaphospholane with 6-aminopenicillanic acid in a molar ratio greater than 1:1 under anhydrous conditions in the presence of an acid binding agent and thereafter acylating the reaction product thus formed with D(-)-phenyl glycyl chloride, hydrochloride and subsequently hydrolyzing the thus formed product with water to obtain a hydrochloride salt of D(-)α-aminobenzylpenicillin.

13. A process for preparing a cephalosporin having antibacterial activity against gram positive and/or gram negative microorganisms, which comprises:
a. reacting a compound selected from the class consisting of 7-aminocephalosporanic acid and 7-amino-3-desacetoxycephalosporanic acid with a phosphorylating compound of the formula:

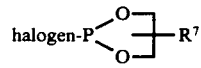

wherein R⁷ is selected from the class consisting of hydrogen and lower alkyl; in the presence of an acid binding agent to form a phosphorus anhydride derivative of said 7-aminocephalosporanic acid or acid 7-amino-3-desacetoxycephalosporanic acid, the molar ratio of said phosphorylating compound to either one of said 7-aminocephalosporanic acid or 7-amino-3-desacetoxycephalosporanic acid being at least about 1:1;
b. reacting said phosphorus anhydride derivative obtained in step (a) with an acylating agent which is a reactive functional derivative of an organic carboxylic acid to form the corresponding N-acylated phosphorus anhydride of said compound obtained in step (b); and
c. subjecting said N-acylated compound obtained in step (b) to hydrolysis to obtain a compound selected from the class consisting of:

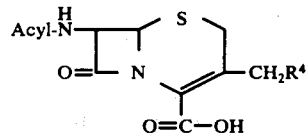

wherein R⁴ is either hydrogen or acetoxy; and an acid addition salt thereof.

14. A process according to claim 11 wherein said acid binding agent is a strong tertiary amine.

15. A process according to claim 14 wherein said acylating reagent is a reactive functional derivative of a compound selected from the class consisting of D(-)phenyl glycine and a thienylacetic acid.

* * * * *